(12) United States Patent
Murugan et al.

(10) Patent No.: US 9,422,230 B2
(45) Date of Patent: Aug. 23, 2016

(54) PROCESS FOR THE PREPARATION OF AN ANTICONVULSANT AGENT PREGABALIN HYDROCHLORIDE

(71) Applicant: Council of Scientific and Industrial Research, New Delhi (IN)

(72) Inventors: Muthukrishnan Murugan, Pune (IN); Mujahid Mohammad, Pune (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 14/890,012

(22) PCT Filed: May 9, 2014

(86) PCT No.: PCT/IN2014/000319
§ 371 (c)(1),
(2) Date: Nov. 9, 2015

(87) PCT Pub. No.: WO2014/181359
PCT Pub. Date: Nov. 13, 2014

(65) Prior Publication Data
US 2016/0122289 A1    May 5, 2016

(30) Foreign Application Priority Data
May 9, 2013   (IN) .......................... 1391/DEL/2013

(51) Int. Cl.
C07C 227/18 (2006.01)
C07C 41/02 (2006.01)
C07C 213/00 (2006.01)
C07C 253/30 (2006.01)
C07C 213/02 (2006.01)

(52) U.S. Cl.
CPC .............. *C07C 227/18* (2013.01); *C07C 41/02* (2013.01); *C07C 213/02* (2013.01); *C07C 253/30* (2013.01)

(58) Field of Classification Search
CPC .. C07C 227/18; C07C 213/02; C07C 253/30; C07C 41/02
USPC ........................................ 562/526
See application file for complete search history.

(56) References Cited

FOREIGN PATENT DOCUMENTS

| WO | WO-01/55090 A1 | 8/2001 |
| WO | WO-2011/141923 A2 | 11/2011 |
| WO | WO-2014/181359 | 11/2014 |

OTHER PUBLICATIONS

"International Application No. PCT/IN2014/000319, International Search Report mailed Sep. 29, 2014", (Sep. 29, 2014), 3 pgs.
Hoekstra, Marvin S., et al., "Chemical Development of CI-1008, an Enantiornerically Pure Anticonvulsant", *Organic Process Research & Development, 1*, (1997), 26-38.
Mujahid, Mohammad, et al., "A New Enantioselective Synthesis of the Anticonvulsant Drug Pregabalin (Lyrica) Based on a Hydrolytic Kinetic Resolution Method", *Chirality, 25*, (2013), 965-969.
Shelke, Shivaji H., et al., "An efficient total synthesis of (±)-pregabalin", *Indian Journal of Chemistry, vol. 51B*, (Apr. 2012), 631-634.

*Primary Examiner* — Sikarl Witherspoon
(74) *Attorney, Agent, or Firm* — Schwegman, Lundberg & Woessner, P.A.

(57) ABSTRACT

An efficient synthesis of the anticonvulsant drug, Pregabalin hydrochloride is described using simple transformations in high enantiopurity (>99% ee) and overall yield of 44 to 50%.

4 Claims, 2 Drawing Sheets

PROCESS FOR THE PREPARATION OF AN ANTICONVULSANT AGENT PREGABALIN HYDROCHLORIDE

PRIORITY CLAIM TO RELATED APPLICATIONS

This application is a U.S. national stage application filed under 35 U.S.C. §371 from International Application Serial No. PCT/IN2014/000319, which was filed 9 May 2014, and published as WO2014/181359 on 13 Nov. 2014, and which claims priority to India Application No. 1391/DEL/2013, filed 9 May 2013, which applications and publication are incorporated by reference as if reproduced herein and made a part hereof in their entirety, and the benefit of priority of each of which is claimed herein.

FIELD OF THE INVENTION

The present invention relates to a process for the preparation of an anticonvulsant agent Pregabalin hydrochloride in good yield and high enantiopurity. The present invention further relates to the synthesis of an anticonvulsant agent Pregabalin hydrochloride starting from commercially available (S)-2-(2-(benzyloxy)ethyl) oxirane.

BACKGROUND OF THE INVENTION

Pregabalin (Lyrica®) is the (S) enantiomer of 3-(aminoethyl)-5-methylhexanoic acid, structurally similar to the neurotransmitter γ-aminobutyric acid (GABA) and a successor to Gabapentin which is a neurontin drug. It is found to be potent for the treatment of neurological related disorders, epilepsy, anxiety and social phobia. Pharmacological studies show that only (S)-enantiomer is responsible for the drug activity, whereas (R)-enantiomer is inactive.

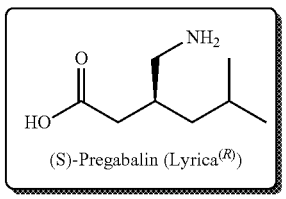

(S)-Pregabalin (Lyrica(R))

Numerous methods describing the synthesis of Pregabalin have been reported.

An Article titled, "*Chemical Development of CI*-1008, *an Enantiomerically Pure Anticonvulsant*" by Marvin S. Hoekstra, Denis M. Sobieray, Mark A. Schwindt, Thomas A. Mulhern, Todd M. Grote, Brian K. Huckabee, Valerie S. Hendrickson, Lloyd C. Franklin, Eric J. Granger, and Gregory L. Karrick in *Organic Process Research & Development* 1997, 1, 26-38, reports the development of a manufacturing process for (S)-3-(aminomethyl)-5-methylhexanoic acid, an anticonvulsant, is described. Initial preparation employed an Evans chiral alkylation on (4R,5S)-4-methyl-3-(1-oxo-4-methylpentyl)-5-phenyl-2-oxazolidinone, using benzyl bromoacetate. Use of tert-butyl bromoacetate, proved advantageous for large-scale preparation. Route selection for a low-cost manufacturing process was based on "ideal process" cost projections. Four routes were evaluated in the laboratory. Of the four, two were scaled up in the pilot plant, resulting in selection of a route based on synthesis of racemic 3-(aminomethyl)-5-methylhexanoic acid, followed by resolution with (S)-(+)-mandelic acid.

Patent no. WO 2011/141923 A2 by Lupin limited discloses a cost effective, ecofriendly process for preparation of enantiomerically pure (S)-3-cyano-5-methyl-hexanoic acid alkyl ester which is an intermediate of γ-amino acids, particularly (S)-Pregabalin.

Patent no. WO 01/55090 A1 by Warner Lambert company discloses a method of making (S)-(+)-3-(aminomethyl)-5-methylhexanoic acid (Pregabalin) or a salt thereof via an asymmetric hydrogenation synthesis. Article titled "An efficient total synthesis of (±) Pregabalin" by Shivajishelke et al. in Indian Journal of Chemistry Vol. 51 B, April 2012, 631-34 discloses preparation of (±) Pregabalin (80%) comprising protection and deprotection of $NH_2$ group by Boc.

Industrially, Pregabalin is prepared using enzymatic resolution method developed by Pfizer. Alternatively, enantiomerically pure Pregabalin can be obtained using diastereomeric resolution methods, different chiral pool approaches starting from L-leucine, D-mannitol & γ-butyrolactones, etc. Further, many enantioselective routes have highlighted in the literature such as asymmetric hydrogenation using rhodium Me-DuPHOS catalyst, Quinine mediated desymmetrization of cyclic anhydride and use of chiral auxiliaries such as, Evan's oxazolidinone and (S)-methylbenzyl amine. One interesting route was developed by Jacobsen and co-workers of conjugate addition of hydrogen cyanide to α, β-unsaturated imide using aluminiumsalen catalyst. Very recently, Li et al reported the synthesis using asymmetric Michael addition of diethyl malonate and nitroalkene under solvent-free conditions using chiral thiourea catalyst. Some of these methods have intrinsic disadvantages such as expensive, commercially unavailable starting materials & catalysts, high catalytic loading, low yield, low stereoselectivity amongst others. In addition, crystallization of intermediates is often required in order to achieve high enantiopurity of final Pregabalin.

Therefore, development of a new practical and expeditious synthesis of Pregabalin is highly desirable.

OBJECT OF THE INVENTION

Main object of the present invention is to provide a process for the synthesis of Pregabalin hydrochloride starting from (S)-2-(2-(benzyloxy)ethyl)oxirane.

SUMMARY OF THE INVENTION

Accordingly, present invention provides a process for the synthesis of (S) Pregabalin hydrochloride of formula S-1

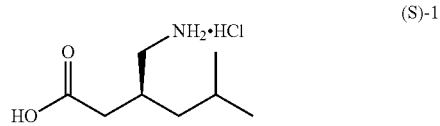

comprising the steps of:
a. subjecting an epoxide of formula (S)-2 to regioselective ring opening with isopropyl magnesium chloride in presence of copper iodide (CuI) to afford a secondary alcohol of formula (R)-3;

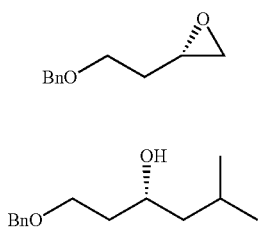

(S)-2

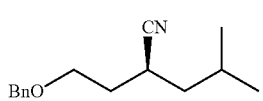

(R)-3 b. subjecting the secondary alcohol of formula (R)-3 as obtained in step (a) to its corresponding mesylate using methanesulfonyl chloride and triethyl amine (TEA) in dichloromethane(DCM) at temperature in the range of 0 to 10° C. followed by displacement using trimethylsilyl cyanide (TMSCN) in presence of tetrabutylammonium fluoride (TBAF) in acetonitrile to obtain a cyano derivative of formula (S)-4;

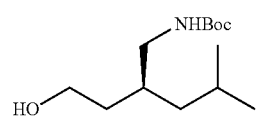

(S)-4 c. subjecting the cyano derivative of formula (S)-4 of step (b) to hydrogenation and concomitant Boc-protection using (Boc)$_2$O and Raney-Ni as a catalyst to furnish a amino alcohol of formula (S)-5;

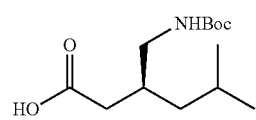

(S)-5 d. oxidizing the amino alcohol of formula (S)-5 of step (c) using sodium chlorite catalyzed by 2,2,6,6-Tetramethyl-1-piperidinyloxy (TEMPO) and bleach at temperature in the range of at 30 to 40° C. to afford a compound of formula (S)-6;

(S)-6 e. subjecting the compound of formula (S)-6 of step (d) for Boc-deprotection using hydrochloride (HCl) and acetone at temperature in the range of 55 to 65° C. to afford Pregabalin hydrochloride of formula (S)-1.

In an embodiment of the present invention, the compound of formula (S)-6 is converted to compound of formula (S)-7 for enentiomeric excess (ee) determination using isobutyl chloroformate and benzylamine.

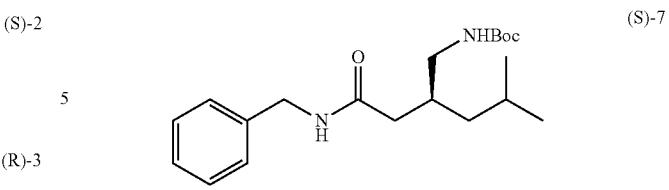

(S)-7

In an embodiment of the present invention, (S)-7 exhibits >99% ee) enantiomeric excess (ee).

In another embodiment of the present invention, yield of the Pregabalin hydrochloride of formula (S)-1 is in the range of 44 to 50%.

In yet another embodiment of the present invention, Pregabalin hydrochloride of formula (S)-1 is obtained in enantioselectivity (>99% ee) $\{[60]_D=+7.8$ (c 1.1, H$_2$O); lit $[\alpha]_D=+7.0$ (c 1.1, H$_2$O)$\}$.

DETAILED DESCRIPTION OF INVENTION

The present invention provides a process for the synthesis of an anticonvulsant agent (S) Pregabalin hydrochloride starting from commercially available (S)-2-(2-(benzyloxy)ethyl) oxirane in good yield and high enantiopurity of 99% ee.

Figure 1:
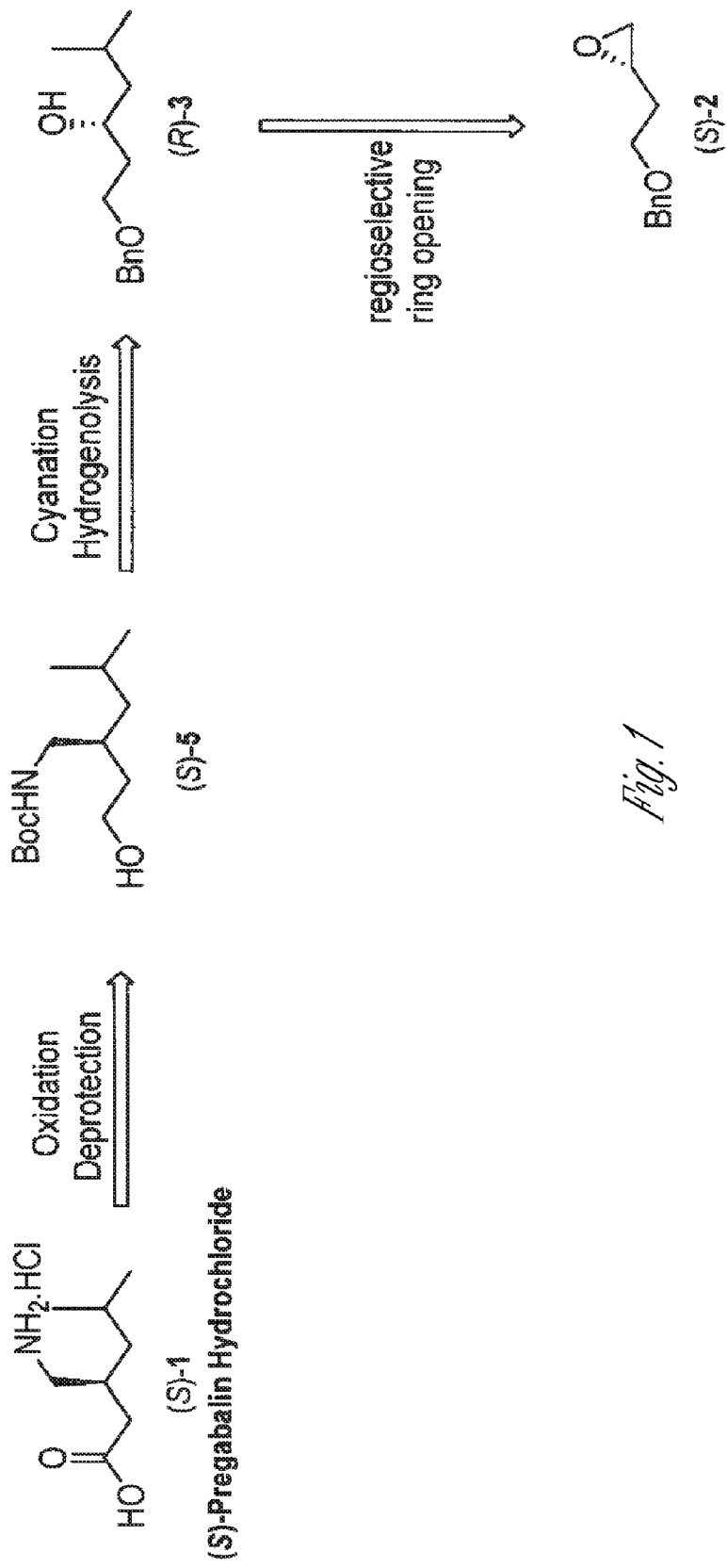
FIG. 1 represents retrosynthetic analysis of Pregabalin hydrochloride of formula (S)-1.

The present invention provides a retrosynthetic analysis of Pregabalin hydrochloride of formula (S)-1 as shown in FIG. 1. The secondary hydroxy compound (R)-3 would serve as a key intermediate for the synthesis which can be extended to the Boc-protected amino alcohol (S)-5 via cyanation and hydrogenation. Simple oxidation and deprotection of compound (S)-5 can lead to the target molecule of formula (S)-1.

Figure 2:
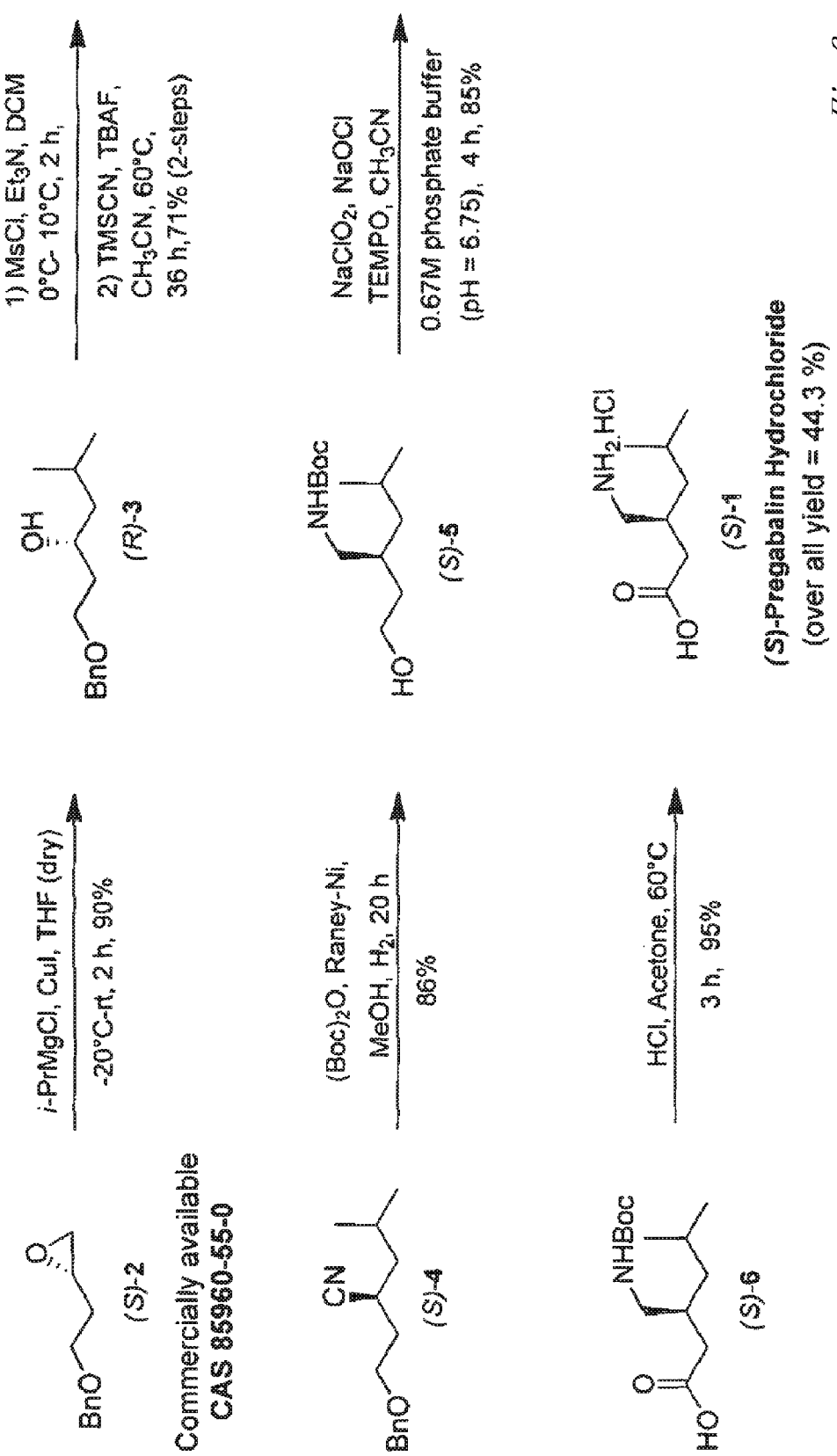
FIG. 2 represents synthesis of Pregabalin hydrochloride of formula (S)-1.

The present invention provides a process for the synthesis of Pregabalin hydrochloride of formula (S)-1 as depicted in FIG. 2, comprising the steps:

a. Subjecting an epoxide of formula (S)-2 to regioselective ring opening with isopropyl magnesium chloride in presence of CuI to afford a secondary alcohol of formula (R)-3 in 90% yield.

b. Mesylation of the secondary alcohol of formula (R)-3 of step (a) to its corresponding mesylate using methanesulfonyl chloride and Et$_3$N in DCM to obtain the crude mesylate which is displaced using TMSCN in presence of TBAF in acetonitrile to furnish the cyano derivative of formula (S)-4 in 71% yield (2-steps).

c. Hydrogenation of compound of formula (S)-4 of step (b) and concomitant Boc-protection using (Boc)$_2$O and Raney-Ni as a catalyst in methanol to furnish amino alcohol of formula (S)-5.

d. Oxidation of compound of formula (5)-5 of step (c) using sodium chlorite catalyzed by TEMPO and bleach in acetonitrile-phosphate buffer (pH 6.8) condition to afford the corresponding acid of formula (S)-6 in 85% yield.

e. Boc-deprotection of (S)-6 using conc HCl/acetone to give the desired product Pregabalin hydrochloride of formula (S)-1 in excellent enantioselectivity (>99% ee) $\{[\alpha]_D=+7.8$ (c 1.1, H$_2$O); lit $[\alpha]_D=+7.0$ (c 1.1, H$_2$O)$\}$.

The structure of Pregabalin hydrochloride of formula (S)-1 was confirmed by its IR, $^1$H NMR, $^{13}$C NMR and mass spectral analysis.

EXAMPLES

The following examples are given by way of illustration therefore should not be construed to limit the scope of the invention.

Experimental

General

Solvents were purified and dried by standard procedures prior to use. Tetrabutylammonium fluoride (TBAF) was used as a 1.0 M solution in THF. Isopropyl magnesium chloride was used as a 2.0 M solution in THF. IR spectra were obtained from Perkin-Elmer Spectrum one spectrophotometer. $^1$H NMR and $^{13}$C NMR spectra were recorded on a Bruker AC-200 NMR spectrometer. Spectra were obtained in CDCl$_3$. Monitoring of reactions was carried out using TLC plates, Merck Silica Gel 60 F254 and visualization with UV light (254 and 365 nm), 12 and anisaldehyde in ethanol as development reagents. Optical rotations were measured with a JASCO P 1020 digital polarimeter. Mass spectra were recorded at ionization energy 70 eV on API Q Star Pulsar spectrometer using electrospray ionization. Enantiomeric excess was determined by chiral HPLC.

Example 1

Preparation of (R)-1-(benzyloxy)-5-methylhexan-3-ol [(R)-3]

To a pre cooled (−20° C.) solution of chiral epoxide of formula (S)-2 (3.8 g, 21.2 mmol) and CuI (0.1 g) in dry THF (30 mL) was added isopropyl magnesium chloride (15.8 mL, 31.8 mmol) in THF for about 15 mins. Subsequently, the reaction mixture was allowed to attain ambient temperature and continued the stirring for additional 2 h. After completion of the reaction (indicated by TLC), 20 ml aqueous NH$_4$Cl was added, after which the reaction mixture was filtered, and washed with ethyl acetate. The solvent was removed under reduced pressure and the crude product was subjected to column chromatography (silica gel, petroleum ether/ethyl acetate, 85:15) to yield (R)-3 as colorless oil. (4.2 g; 90%) [α]$^{25}_D$=+17.5 (c 2.2, CHCl$_3$); IR (CHCl$_3$, cm$^{-1}$): υ$_{max}$ 3502, 3018, 2957, 1603, 1454, 1366, 1307, 1092; NMR (200 MHz, CDCl$_3$): δ$_H$ 0.91 (d, J=6.6 Hz, 6H), 1.12-1.29 (m, 1H), 1.38-1.58 (m, 1H), 1.73 (dd, J=11.7, 5.6 Hz, 2H), 1.74-1.85 (m, 1H), 2.84 (bd, J=2.6 Hz, 1H), 3.60-3.78 (m, 2H), 3.82-3.96 (m, 1H), 4.53 (s, 2H), 7.27-7.37 (m, 5H); $^{13}$C NMR (50 MHz, CDCl$_3$): δ$_c$ 138.0 (C), 128.5 (CH, 2 carbons), 127.7 (CH, 3 carbons), 73.4 (CH$_2$), 69.4 (CH), 69.3 (CH$_2$), 46.7 (CH$_2$), 36.9 (CH$_2$), 24.5 (CH), 23.4 (CH$_3$), 22.2 (CH$_3$); MS: m/z 245 [M+Na]$^+$.

Example 2

Preparation of (S)-2-(2-(benzyloxy)ethyl)-4-methylpentanenitrile [(S)-4]

To a pre cooled (0° C.) solution of the alcohol of formula (R)-3 (4.0 g, 17.9 mmol) in dry DCM (50 mL) was added triethylamine (5.4 mL, 39.3 mmol) followed by slow addition of methanesulfonyl chloride (19.6 mmol, 1.5 mL) dropwise. The reaction mixture was stirred at 10° C. for 2 hours before quenching, with water, 10 ml DCM was added mention amount here and extracted with water, washed with brine and evaporated under reduced pressure. The crude product was used for next step without purification. Trimethylsilyl cyanide (3.3 mL, 26.8 mmol and TBAF (26.7 mL, 26.8 mmol) were added to a stirring solution of crude mesylated product as obtained above in acetonitrile under an atmosphere of nitrogen at room temperature i.e. 30° C. The reaction mixture was stirred at 60° C. for 24 hours. After completion of the reaction (indicated by TLC), solvent was removed and the crude product was subjected to column chromatography (silica gel, petroleum ether/ethyl acetate, 92:8) to yield (S)-4 as a colorless oil. (2.9 g; 71%, 2 steps)

[α]$^{25}_D$=+17.9 (c 1.08, CHCl$_3$); IR (CHCl$_3$, cm$^{-1}$): υ$_{max}$ 3421, 2958, 2871, 2236, 1603, 1496, 1455, 1368, 1116; NMR (200 MHz, CDCl$_3$): δ$_H$ 0.92 (d, J=5.2 Hz, 3H), 0.95 (d, J=5.4 Hz, 3H), 1.23-1.37 (m, 1H), 1.53-1.67 (m, 1H), 1.76-1.97 (m, 3H), 2.79-2.94 (m, 1H), 3.63 (apparent t, J=6.1 Hz, 2H), 4.53 (d, J=11.8 Hz, 2H), 7.26-7.41 (m, 5H); $^{13}$C NMR (50 MHz, CDCl$_3$): δ$_c$ 138.0 (C), 128.5 (CH, 2 carbons), 127.7 (CH, 3 carbons), 122.1 (C), 73.3 (CH$_2$), 66.9 (CH$_2$), 41.2 (CH$_2$), 33.0 (CH$_2$), 26.7 (CH), 26.2 (CH), 23.0 (CH$_3$), 21.5 (CH$_3$); MS: m/z 254 [M+Na]$^+$.

Example 3

Preparation of (S)-tert-butyl (2-(2-hydroxyethyl)-4-methylpentyl)carbamate [(S)-5]

To a solution of (S)-4 (2.0 g, 8.6 mmol) and Boc$_2$O (2.0 g, 9.5 mmol) in methanol (30 mL) was added activated Raney-nickel catalyst (200 mg) and the reaction mixture was stirred under hydrogen (60 psi) for 20 h. After completion of the reaction (indicated by TLC), filtered the catalyst over a plug of celite bed (EtOAc eluent) and the solvent was evaporated under reduced pressure. The crude product was purified by column chromatography (silica gel, petroleum ether/ethyl acetate, 70:30) to yield (S)-5 as colorless oil (1.8 g, 86%);

[α]$^{25}_D$=+1.8 (c=1.4, CHCl$_3$); IR (CHCl$_3$, cm$^{-1}$): υ$_{max}$ 3457, 3019, 2959, 2931, 1698, 1513, 1393, 1367, 1168; NMR (200 MHz, CDCl$_3$): δ$_H$ 0.88 (apparent t, J=6.2 Hz, 6H), 1.06-1.18 (m, 2H), 1.44 (s, 9H), 1.47-1.74 (m, 4H), 2.25 (bs, 1H), 3.10 (apparent t, J=5.6 Hz, 2H), 3.65-3.79 (m, 2H), 4.80 (bs, 1H); $^{13}$C NMR (50 MHz, CDCl$_3$): δ$_c$ 156.5 (CO), 79.5 (C), 60.7 (CH$_2$), 44.0 (CH$_2$), 42.0 (CH$_2$), 34.7 (CH$_2$), 33.6 (CH), 28.4 (CH$_3$, 3 carbons), 25.2 (CH), 22.8 (CH$_3$), 22.7 (CH$_3$); MS: m/z 268 [M+Na]$^+$.

Example 4

Preparation of (S)-3-(((tert-butoxycarbonyl)amino)methyl)-5-methylhexanoic acid [(S)-6]

A mixture of (S)-5 (1 g, 4.0 mmol), TEMPO (0.05 g, 0.32 mmol), acetonitrile (20 mL), and sodium phosphate buffer (16 mL, 0.67 M, pH 6.7) was heated to 35° C. Then sodium chlorite (1.32 g dissolved in 2 mL water, 14.6 mmol) and dilute bleach (4-6%, 1 mL diluted in 2 mL water) were added simultaneously over 1 h. The reaction mixture was stirred at 35° C. until the reaction is complete (6 h, TLC), then cooled to room temperature i.e. 30° C. Water (30 mL) was added and the pH is adjusted to 8 with 2 N NaOH. The reaction is quenched by pouring into ice cold Na$_2$SO$_3$ solution maintained at <20° C. After stirring for 30 min at room temperature i.e. 30° C., ethyl acetate (30 mL) was added and continued the stirring for additional 15 min. The organic layer was separated and discarded. More ethyl acetate (30 mL) was added, and the aqueous layer was acidified with 2N HCl to pH 4 mention exact value. The organic layer was separated, washed with water (2×15 mL), brine (20 mL) and concentrated under reduced pressure to afford the carboxylic acid (S)-6 (0.88 g, 85%).

$[\alpha]^{25}_D$=−8.6 (c 1.1, CHCl$_3$) {lit. $[\alpha]^{25}_D$=1.4 (c 3.3, EtOH)}; IR (CHCl$_3$, cm$^{-1}$): $\upsilon_{max}$ 3450, 3020, 2927, 1646, 1521, 1423; NMR (200 MHz, CDCl$_3$): $\delta_H$ 0.90 (apparent t, J=6.8 Hz, 6H), 1.16-1.19 (m, 2H), 1.45 (s, 9H), 1.62-1.69 (m, 1H), 2.10-2.35 (m, 3H), 3.05-3.09 (m, 1H), 3.21-3.25 (m, 1H), 4.78 (bs, 1H); $^{13}$C NMR (50 MHz, CDCl$_3$): $\delta_c$ 177.8 (CO), 156.5 (CO), 79.7 (C), 43.8 (CH$_2$), 41.4 (CH$_2$), 37.1 (CH$_2$), 33.8 (CH), 28.4 (CH$_3$, 3 carbons), 25.2 (CH), 22.7 (CH$_3$, 2 carbons); MS: m/z 282 [M+Na]$^+$.

Example 5

Preparation of (S)-3-(aminomethyl)-5-methylhexanoic acid hydrochloride [(S)-1]

To a solution of compound (S)-6 (0.25 g, 1 mmol) in acetone (10 mL) was added HCl (1 mL) and the reaction mixture was stirred at 60° C. for 3 hours, after which the solvent was evaporated under reduced pressure. Water (10 mL) was added and extracted with DCM. Aqueous layer was heated followed by filtration through Celite bed and concentrated under reduced pressure furnished a residue, which was dried at 50° C. for more than 48 hours to afford Pregabalin hydrochloride of formula (S)-1 (0.18 g, 95%).

$[\alpha]^{25}_D$=+7.8 (c 1.1, H$_2$O) {lit. $[\alpha]^{25}_D$=+7.0 (c 1.03, H$_2$O)}; IR (Neat, cm$^{-1}$): $\upsilon_{max}$ 3448, 3211, 3130, 1720, 1431, 1215; NMR (200 MHz, D$_2$O): $\delta_H$ 0.87 (d, J=4.7 Hz, 3H), 0.90 (d, J=4.6 Hz, 3H), 1.25 (apparent t, J=6.7 Hz, 2H), 1.58-1.75 (m, 1H), 2.22-2.28 (m, 1H), 2.50 (m, 2H), 3.02 (d, J=5.6 Hz, 2H); $^{13}$C NMR (50 MHz, CD$_3$OD): $\delta_c$ 175.7 (CO), 44.2 (CH$_2$), 41.7 (CH$_2$), 37.0 (CH$_2$), 32.3 (CH), 25.8 (CH), 22.9 (CH$_3$), 22.2 (CH$_3$); MS: m/z 160 [M+H]$^+$.

Example 6

Preparation of (S)-tert-butyl (2-(2-(benzylamino)-2-oxoethyl)-4-methylpentyl)carbamate [(S)-7]

For purpose of ee determination Boc-protected acid was converted to N-benzyl amide ((S)-7).

To a solution of acid (S)-6 (0.11 g, 0.42 mmol) in dry THF was added N-methylmorpholine (0.05 mL, 0.46 mmol) at −78° C. under argon atmosphere. After 5 min, isobutyl chloroformate (0.06 mL, 0.46 mmol) was added and stirred the content for another 5 min. To this reaction mixture benzylamine (0.05 mL, 0.46 mmol) was added at −78° C. and allowed the reaction mixture to stir at room temperature i.e. 30° C. for 2 h. After completion of the reaction, reaction mixture was filtered, washed with ethyl acetate. The solvent was removed under reduced pressure and the crude product was subjected to column chromatography (silica gel, petroleum ether/ethyl acetate, 65:35) to yield N-benzyl amide (S)-7 (0.12 g, 85%) $[\alpha]^{25}_D$=−3.5 (c 0.8, CHCl$_3$) ee>99%; The enantiomeric ratio was determined by chiral HPLC: Chiralcel OJ-H (250×4.6 mm), Pet ether: Ethanol (90:10).

Wavelength-220 nm, Flow-0.5 mL/min. (R)-isomer-Retention time: 8.208 min; (S)-isomer-Retention time: 8.808 min.

ADVANTAGES OF THE INVENTION 1. (S) Pregabalin, enantiomer of 3-(aminoethyl)-5-methylhexanoic acid, is structurally similar to the neurotransmitter γ-aminobutyric acid (GABA) and a successor to Gabapentin which is a neurontin drug.
2. Novel route of synthesis
3. Commercially available starting material
4. The compound has potential in the treatment of neurological related disorders, epilepsy, anxiety and social phobia.
5. High enantiopurity (>99%) and good overall yield (45%).

We claim:
1. A process for the synthesis of Pregabalin hydrochloride formula S-1

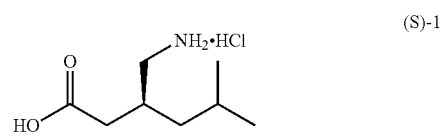

comprising the steps of:
a. subjecting an epoxide of formula (S)-2 to regioselective ring opening with isopropyl magnesium chloride in presence of copper iodide (CuI) to afford a secondary alcohol of formula (R)-3;

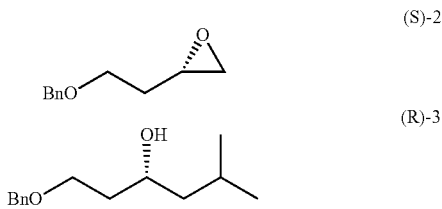

b. subjecting the secondary alcohol of formula (R)-3 as obtained in step (a) to its corresponding mesylate using methanesulfonyl chloride and triethyl amine (TEA) in dichloromethane(DCM) at temperature in the range of 0 to 10° C. followed by displacement using trimethylsilyl cyanide (TMSCN) in presence of tetrabutylammonium fluoride (TBAF) in acetonitrile to obtain a cyano derivative of formula (S)-4;

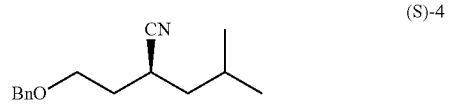 [SMILES: CC(C)C[C@H](C#N)CCOCc1ccccc1]

c. subjecting the cyano derivative of formula (S)-4 of step (b) to hydrogenation and concomitant Boc-protection using (Boc)$_2$O and Raney-Ni as a catalyst to furnish a amino alcohol of formula (S)-5;

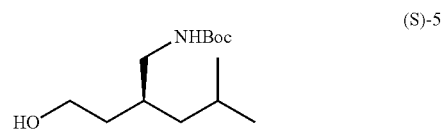

d. oxidizing the amino alcohol of formula (S)-5 of step (c) using sodium chlorite catalyzed by 2,2,6,6-Tetramethyl- 1-piperidinyloxy (TEMPO) and bleach at temperature in the range of at 30 to 40° C. to afford a compound of formula (S)-6;

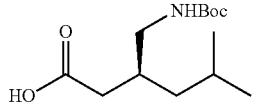
(S)-6 e. subjecting the compound of formula (S)-6 of step (d) for Boc-deprotection using hydrochloride (HCl) and acetone at temperature in the range of 55 to 65° C. to afford Pregabalin hydrochloride of formula (S)-1.

2. The process according to claim 1, wherein Pregabalin hydrochloride of formula (S)-1 is prepared with yield in the range of 44 to 50%.

3. The process according to claim 1, wherein the compound of formula (S)-6 is converted to compound of formula (S)-7 for enantiomeric excess (ee) determination of Pregabalin hydrochloride using isobutyl chloroformate and benzylamine

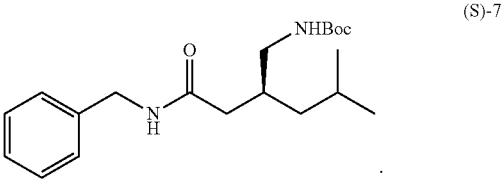 [SMILES: CC(C)C[C@H](CNC(=O)OC(C)(C)C)CC(=O)NCc1ccccc1]
(S)-7

4. The process according to claim 1, wherein (S)-7 exhibits >99% enantiomeric excess (ee).

* * * * *